(12) United States Patent
Denny et al.

(10) Patent No.: US 8,922,367 B2
(45) Date of Patent: Dec. 30, 2014

(54) SYSTEM AND METHOD FOR MEDICAMENT STORAGE, DISPENSING, AND ADMINISTRATION

(71) Applicant: Mylan, Inc., Morgantown, WV (US)

(72) Inventors: John W. Denny, Morgantown, WV (US); Kevin Ostrander, Ringoes, NJ (US)

(73) Assignee: Mylan, Inc., Morgantown, WV (US)

( * ) Notice: Subject to any disclaimer, the term of this patent is extended or adjusted under 35 U.S.C. 154(b) by 0 days.

(21) Appl. No.: 14/282,884

(22) Filed: May 20, 2014

(65) Prior Publication Data

US 2014/0252927 A1     Sep. 11, 2014

Related U.S. Application Data

(63) Continuation-in-part of application No. PCT/US2013/072878, filed on Dec. 3, 2013.

(60) Provisional application No. 61/732,753, filed on Dec. 3, 2012.

(51) Int. Cl.
| | | |
|---|---|---|
| *G08B 1/08* | (2006.01) | |
| *B65D 83/02* | (2006.01) | |
| *A61M 5/50* | (2006.01) | |
| *A61M 5/20* | (2006.01) | |

(52) U.S. Cl.
CPC ............. *B65D 83/02* (2013.01); *A61M 5/5086* (2013.01); *A61M 5/20* (2013.01)
USPC ................... 340/539.12; 340/691.1; 340/500; 340/5.73; 604/500; 604/134; 604/59; 206/363

(58) Field of Classification Search
USPC .......... 340/539.12, 691.1, 500, 5.73, 5.2, 5.3; 604/500, 65, 134, 59, 60, 93.01; 700/236, 244, 237; 221/25, 71, 2; 206/363–365
See application file for complete search history.

(56) References Cited

U.S. PATENT DOCUMENTS 4,663,621 A * 5/1987 Field et al. ...................... 340/5.3
4,731,765 A * 3/1988 Cole et al. ........................ 368/10
(Continued)

FOREIGN PATENT DOCUMENTS

| EP | 1291802 A2 | 3/2003 |
|---|---|---|
| WO | 9621925 A1 | 7/1996 |

(Continued)

OTHER PUBLICATIONS

"International Search Report for PCT/US2013/072878 dated Feb. 26, 2014".

*Primary Examiner* — Hoi Lau
(74) *Attorney, Agent, or Firm* — Kramer Amado, P.C.

(57) ABSTRACT

Various exemplary embodiments relate to a medicament storage case including: a case body securable to a wall; a door connected to the body; a sleeve to contain an epinephrine injector; a medicament lock including a hook, wherein the hook is positioned to engage the sleeve when in a first position and is positioned to disengage the sleeve when in a second position; an actuator including a solenoid, wherein the solenoid, upon activation, moves the hook from the first position to the second position; a microphone configured to receive first audio as input; a speaker configured to output second audio; a communication unit configured to provide Internet connectivity; a button; and a processor configured to: in response to pressing the button: establish communication between the local user and a remote site, receive an unlock message, and in response to receiving the unlock message, activate the solenoid to release of the sleeve.

21 Claims, 10 Drawing Sheets

(56) References Cited

U.S. PATENT DOCUMENTS

| | | | |
|---|---|---|---|
| 5,221,024 A * | 6/1993 | Campbell | 221/3 |
| 5,710,551 A * | 1/1998 | Ridgeway | 340/870.09 |
| 5,815,586 A * | 9/1998 | Dobbins | 381/124 |
| 5,835,455 A * | 11/1998 | Hanson et al. | 368/10 |
| 5,967,975 A | 10/1999 | Ridgeway | |
| 6,109,774 A * | 8/2000 | Holmes et al. | 700/231 |
| 6,158,613 A | 12/2000 | Novosel et al. | |
| 6,401,991 B1 * | 6/2002 | Eannone | 222/638 |
| 6,471,087 B1 * | 10/2002 | Shusterman | 221/2 |
| 6,633,796 B1 | 10/2003 | Pool et al. | |
| 6,707,763 B2 | 3/2004 | Osberg et al. | |
| 6,825,753 B2 * | 11/2004 | Cardinale et al. | 340/5.73 |
| 6,880,722 B2 * | 4/2005 | Anderson et al. | 221/71 |
| 6,937,150 B2 | 8/2005 | Medema et al. | |
| 6,941,274 B1 * | 9/2005 | Ramachandran et al. | 705/26.35 |
| 7,715,277 B2 * | 5/2010 | de la Huerga | 368/10 |
| 7,749,194 B2 * | 7/2010 | Edwards et al. | 604/131 |
| 7,941,534 B2 * | 5/2011 | de la Huerga | 709/225 |
| 8,487,738 B2 * | 7/2013 | Faries et al. | 340/5.2 |
| 8,544,645 B2 * | 10/2013 | Edwards et al. | 206/364 |
| 8,593,278 B2 * | 11/2013 | Churbock et al. | 340/539.29 |
| 8,744,620 B2 * | 6/2014 | Shavelsky et al. | 700/237 |
| 8,753,308 B2 * | 6/2014 | Palmer et al. | 604/59 |
| 2002/0100472 A1 * | 8/2002 | Casper et al. | 128/200.23 |
| 2003/0023146 A1 * | 1/2003 | Shusterman | 600/300 |
| 2003/0090364 A1 * | 5/2003 | Cardinale et al. | 340/5.54 |
| 2004/0099676 A1 * | 5/2004 | Anderson et al. | 221/25 |
| 2004/0158350 A1 * | 8/2004 | Ostergaard et al. | 700/231 |
| 2005/0005934 A1 * | 1/2005 | Harvey | 128/203.15 |
| 2005/0146419 A1 * | 7/2005 | Porter | 340/5.73 |
| 2007/0186923 A1 * | 8/2007 | Poutiatine et al. | 128/200.14 |
| 2007/0197968 A1 * | 8/2007 | Pongpairochana et al. | 604/131 |
| 2007/0204497 A1 * | 9/2007 | de la Huerga | 40/630 |
| 2007/0233001 A1 * | 10/2007 | Burroughs et al. | 604/131 |
| 2008/0249468 A1 * | 10/2008 | Edwards et al. | 604/140 |
| 2009/0120962 A1 * | 5/2009 | Malorni et al. | 222/153.11 |
| 2009/0184022 A1 * | 7/2009 | Coe et al. | 206/531 |
| 2009/0187274 A1 * | 7/2009 | Higham | 700/237 |
| 2010/0022953 A1 * | 1/2010 | Bochenko et al. | 604/134 |
| 2010/0022987 A1 * | 1/2010 | Bochenko et al. | 604/500 |
| 2010/0160857 A1 * | 6/2010 | Pongpairochana et al. | 604/93.01 |
| 2010/0204659 A1 * | 8/2010 | Bochenko et al. | 604/232 |
| 2010/0305750 A1 * | 12/2010 | Conley | 700/237 |
| 2010/0318035 A1 * | 12/2010 | Edwards et al. | 604/187 |
| 2011/0166700 A1 * | 7/2011 | Dunn | 700/237 |
| 2011/0234419 A1 * | 9/2011 | Churbock et al. | 340/691.1 |
| 2012/0259456 A1 * | 10/2012 | Saltsov | 700/237 |
| 2012/0259458 A1 * | 10/2012 | Barrett et al. | 700/237 |
| 2012/0274196 A1 * | 11/2012 | Arceta et al. | 312/249.11 |
| 2013/0030566 A1 * | 1/2013 | Shavelsky et al. | 700/244 |
| 2013/0090594 A1 * | 4/2013 | Palmer et al. | 604/60 |
| 2013/0131586 A1 * | 5/2013 | Poutiatine et al. | 604/59 |
| 2013/0166066 A1 * | 6/2013 | Dunn | 700/236 |
| 2014/0114277 A1 * | 4/2014 | Eggert et al. | 604/500 |

FOREIGN PATENT DOCUMENTS

| | | |
|---|---|---|
| WO | 03043684 A1 | 5/2003 |
| WO | 2005004961 A1 | 1/2005 |
| WO | 2007081947 A2 | 7/2007 |

* cited by examiner

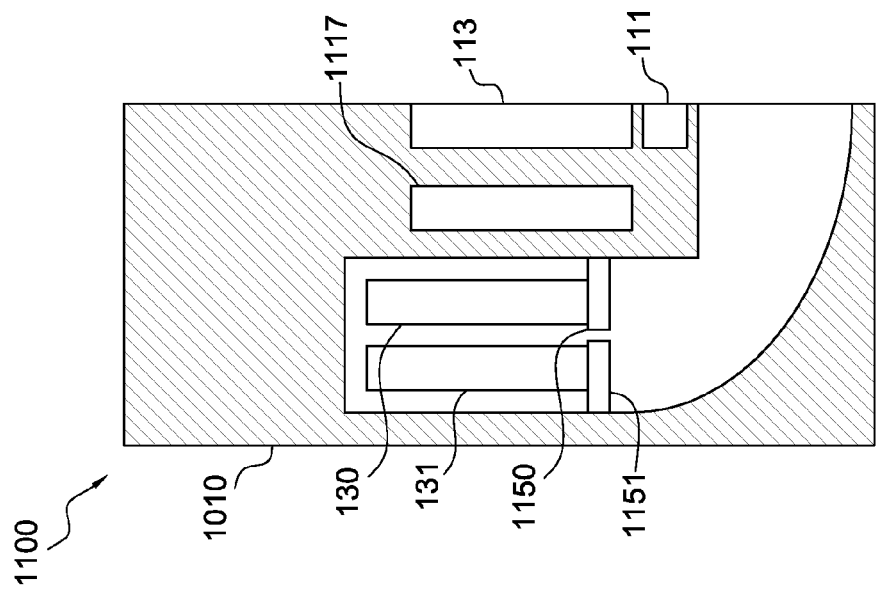
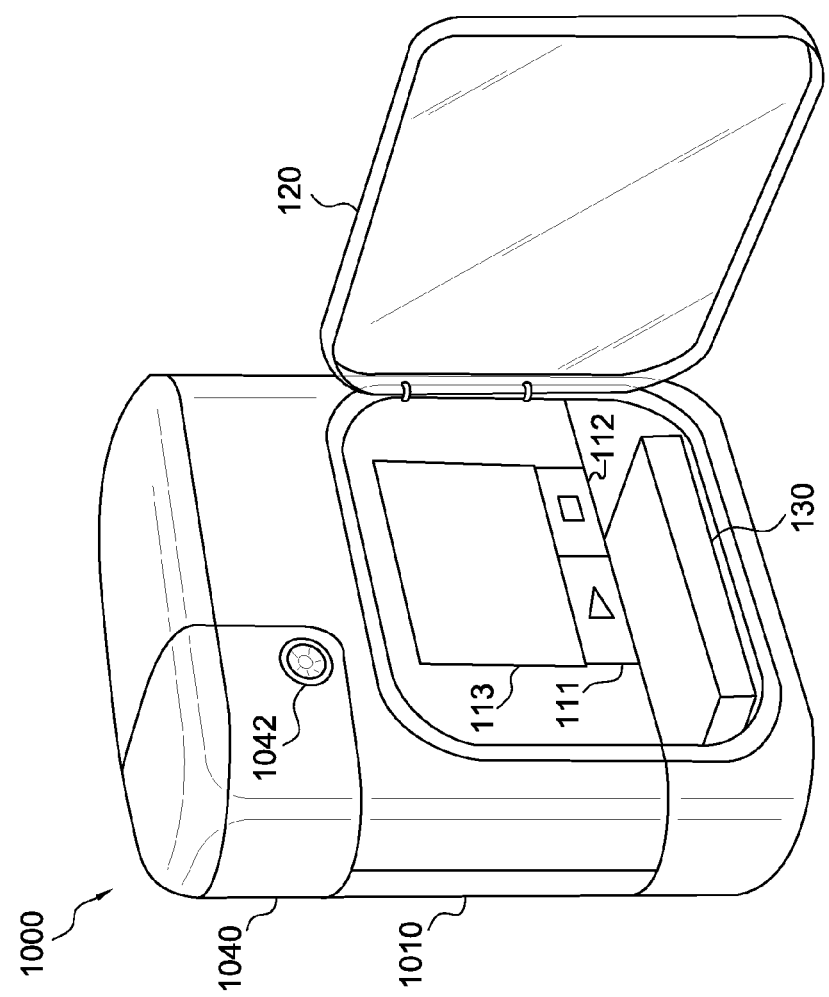

SYSTEM AND METHOD FOR MEDICAMENT STORAGE, DISPENSING, AND ADMINISTRATION

CROSS-REFERENCE TO RELATED APPLICATIONS

This patent application is a continuation-in-part of PCT application number PCT/US2013/072878, filed on Dec. 3, 2013; which claims priority to U.S. provisional patent application No. 61/732,753, filed on Dec. 3, 2012; the entire disclosures of which are hereby incorporated herein for all purposes.

TECHNICAL FIELD

Various exemplary embodiments disclosed herein relate generally to storage, distribution, and administration of medicaments.

BACKGROUND

Some people suffer from medical conditions that may give rise to emergency situations where prompt administration of a medication is of paramount importance. For example, a person with severe allergies exposed to a trigger substance may develop anaphylaxis. Due to its rapid onset and accompanying possibility of death depending on the allergy severity, it is important to administer treatment, such as a dose of epinephrine, as soon as possible. Patients with known allergies are commonly prescribed an auto-injector of epinephrine to treat sudden anaphylaxis, with the plan that the patient will carry the auto-injector with them at all times such that it is always accessible in an emergency situation. Similarly, patients with other medical conditions that may give rise to an emergency situation requiring immediate treatment may be prescribed appropriate medicines or devices to keep on their person.

SUMMARY

In light of the present need for various contingency plans in the administration of epinephrine and other medications and devices, a brief summary of various exemplary embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

Various embodiments relate to a medicament storage case assembly including: a case body defining a front surface, a rear surface, an internal area, and an opening in the front surface through which the internal area is accessible; securing hardware capable of securing the rear surface of the case body to a wall; a door hingedly connected to the case body adjacent the opening, wherein the door blocks access to the internal area when the door occupies a closed position and permits access to the internal area when the door occupies an open position; a medicament lock disposed within the internal area and configured to occupy a locked state and an unlocked state, wherein the medicament lock restricts removal of an epinephrine injector from the internal area when the medicament lock occupies the locked state and allows removal of the epinephrine injector from the internal area when the medicament lock occupies the unlocked state; an actuator configured to transition the medicament lock from the locked state to an unlocked state, wherein transitioning the medicament lock releases the epinephrine injector for removal from the internal area and subsequent use; a microphone configured to receive first audio as input from a local user; a speaker configured to output second audio to the local user; a communication unit configured to provide at least one communication channel to at least one remote site; and a processor configured to: establish, via the communication unit, a two way communication session between the local user and the remote site, wherein the communication unit transmits the first audio received by the microphone and receives the second audio to be output via the speaker, and receive an unlock signal that instructs the storage case to allow access to the epinephrine injector.

Various embodiments relate to a medicament storage case including: a case body defining a front surface, a rear surface, an internal area, and an opening in the front surface through which the internal area is accessible; securing hardware capable of securing the rear surface of the case body to a wall; a door hingedly connected to the case body adjacent the opening, wherein the door blocks access to the internal area when the door occupies a closed position and permits access to the internal area when the door occupies an open position; a retaining structure configured to occupy a first state and a second state, wherein the retaining structure restricts removal of an epinephrine injector from the internal area when the retaining structure occupies the first state and allows removal of the epinephrine injector from the internal area when the retaining structure occupies the second state, wherein the retaining structure transitions from the first state to the second state in response to receiving an unlock signal; a microphone configured to receive first audio as input from a local user; a speaker configured to output second audio to the local user; a communication unit configured to provide at least one communication channel to at least one remote site; and a processor configured to: establish, via the communication unit, a two way communication session between the local user and the remote site, wherein the communication unit transmits the first audio received by the microphone and receives the second audio to be output via the speaker, and receive an access signal that instructs the storage case to allow access to the epinephrine injector.

Various embodiments relate to a medicament storage case including: a case body defining a front surface, a rear surface, an internal area, a lower ledge, and an opening in the front surface through which the internal area is accessible; securing hardware capable of securing the rear surface of the case body to a wall; a door hingedly connected to the case body adjacent the opening, wherein the door blocks access to the internal area when the door occupies a closed position and permits access to the internal area when the door occupies an open position; a sleeve sized to contain an epinephrine injector and located within the internal area, the sleeve including a rail; a medicament lock including a hook movable between a first position and a second position, wherein the hook is positioned to engage the rail of the sleeve when in the first position and is positioned to disengage the rail of the sleeve when in the second position, and wherein the sleeve is suspended above the lower ledge when the hook is engaged with the rail of the sleeve and wherein the sleeve falls to the lower ledge when the hook disengages the rail of the sleeve; an actuator including a solenoid, wherein the solenoid, upon activation, moves the hook from the first position to the second position; a microphone configured to receive first audio as input from a local user; a speaker configured to output second audio to the local user; a communication unit configured to provide plain ordinary telephone system (POTS) connectivity and Internet connectivity; a button accessible to the local user; and a processor configured to: detect a press of the button, in response to detecting the press of the button: establish a telephone call to an emergency dispatch via the communication unit and the POTS, transmit predetermined information to the emergency dispatch via the telephone call, and establish a two-way communication between the local user and a remote site via the communication unit and the Internet, wherein the communication unit transmits the first audio received by the microphone and receives the second audio to be output via the speaker, receive an unlock message via the Internet, and in response to receiving the unlock message, cause activation of the solenoid to effect release of the sleeve.

Various embodiments are described wherein the processor is further configured to output an access signal to the actuator in response to receiving the unlock signal, wherein the actuator transitions the medicament lock from the locked state to the unlocked state in response to receiving the access signal.

Various embodiments additionally include a button in communication with the processor, wherein the processor is configured to establish the two way communication session in response to the button being pressed.

Various embodiments are described wherein the processor is further configured to: establish a landline telephone call via the communication unit and a plain ordinary telephone system (POTS) to an emergency dispatch in response to the button being pressed; and transmit predetermined information to the emergency dispatch via the landline telephone call.

Various embodiments additionally include a display device, wherein the processor is further configured to output video instructions via the display device to the user upon allowing access to the epinephrine injector.

Various embodiments additionally include a sleeve sized to contain the epinephrine injector and located within the internal area, wherein the medicament lock engages the sleeve in the locked state to restrict removal of the epinephrine injector from the internal area and disengages from the sleeve in the unlocked state to allow removal of the epinephrine injector from the internal area.

Various embodiments are described wherein upon the medicament lock disengaging from the sleeve, the sleeve falls away from the medicament lock and toward the opening.

Various embodiments additionally include an additional medicament lock configured to selectively restrict or allow removal of an additional epinephrine injector.

Various embodiments additionally include an additional sleeve including an additional rail; an additional medicament lock engaged with the additional sleeve; an additional solenoid configured to effect disengagement of the additional medicament lock from the additional sleeve; wherein, in causing activation of the solenoid, the processor is configured to determine that the message is applicable to the sleeve and inapplicable to the additional sleeve.

Various embodiments additionally include a detachable device connected to the case body, the detachable device including: the microphone and the speaker; and a WiFi device configured to transmit the video data to the processor.

Various embodiments are described wherein the detachable device is selectively securable to the case body such that, when secured, the detachable device may not be detached from the case body; and the processor is further configured to: receive, via the communication unit, an instruction to release the detachable device, and in response to the instruction to release the detachable device, effect release of the detachable device to allow a user to detach the detachable device from the case body.

Various embodiments are described wherein the processor is further configured to transmit, via the communication module, an indication that the epinephrine injector has been dispensed.

Various embodiments additionally include a temperature sensor for sensing temperature data, wherein the processor is further configured to transmit the temperature data via the communication module.

BRIEF DESCRIPTION OF THE DRAWINGS

In order to better understand various exemplary embodiments, reference is made to the accompanying drawings, wherein:

FIG. 10 illustrates a first alternative embodiment of a medicament storage case;

FIG. 11 illustrates a cross-section of the first alternative embodiment of a medicament storage case;

DETAILED DESCRIPTION

Figure 1:
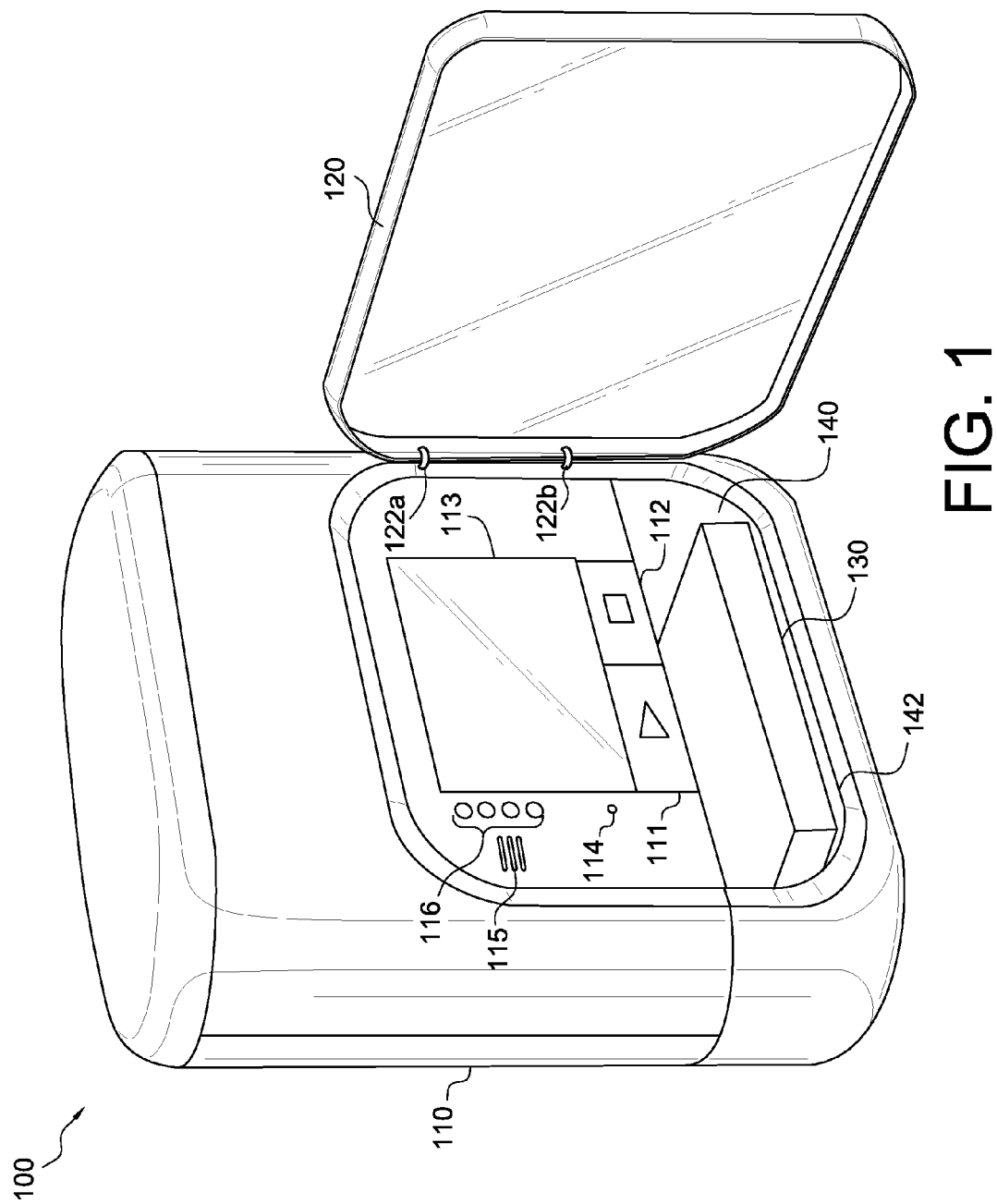
FIG. 1 illustrates an exemplary medicament storage case.

While often effective, the emergency plan of providing a patient with medication to carry at all times is not a complete solution. There are many situations where a patient may not have access to the appropriate medication to address an emergency situation. For example, where the patient's condition is as-yet undiagnosed, there has been no opportunity to prescribe the emergency medication or device in advance. As another example, where the patient is a child or otherwise requires supervision or guidance in use of the medication or device, the patient may not actually carry the prescription which therefore may not be available. Furthermore, the appropriate supervisor for administration may be unavailable. Outside of special circumstances such as these, the patient may simply have forgotten the prescription or otherwise may not currently have the prescribed medication or device with them at the time of the emergency. For at least these reasons, there is a need for an alternative or supplemental solution to providing appropriate prescribed medication or devices in the event of an emergency.

As will be explained in greater detail below, various embodiments include a medicament storage case that restricts access to a stored medicament until an instruction is received from a remote operator, such as an on-call physician, to release the medicament for use by a local patient or other user. To enable the remote operator to adequately determine whether and when it is appropriate to dispense a medicament from the storage case, the storage case additionally facilitates two-way communication with the remote operator. Through this communication, the remote operator may obtain information regarding the patient and the situation sufficient to make a determination of whether medicament should be dispensed.

The description and drawings presented herein illustrate various principles. It will be appreciated that those skilled in the art will be able to devise various arrangements that, although not explicitly described or shown herein, embody these principles and are included within the scope of this disclosure. As used herein, the term, "or," as used herein, refers to a non-exclusive or (i.e., or), unless otherwise indicated (e.g., "or else" or "or in the alternative"). Additionally, the various embodiments described herein are not necessarily mutually exclusive and may be combined to produce additional embodiments that incorporate the principles described herein. It will be apparent that the methods and devices described herein may be used for dispensing medications, medical devices, and combinations thereof. Accordingly, the term "medicament" as used herein will be understood to encompass both medications and medical devices. Further, it will be appreciated with various devices described herein may be used for providing controlled access to substances, devices, and other items outside of the medical field.

Referring now to the drawings, in which like numerals refer to like components or steps, there are disclosed broad aspects of various exemplary embodiments.

FIG. 1 illustrates an exemplary medicament storage case 100. The various embodiments of medicament storage cases disclosed herein, including the exemplary case 100 may also be referred to as medical management systems. As shown, the storage case 100 includes a case body 110 and a door 120 attached thereto by hinges 122a, 122b. The case body 110 includes an interior area 140 that is accessible via an opening in the front surface of the case body 110. In various embodiments, the storage case 100 is mountable to a wall or other structure. As such, the storage case may also include securing hardware sufficient to accomplish such mounting. For example, the rear surface of the case body 110 may include recesses for receiving bolt heads of bolts that have been screwed into a wall. As another example, the securing hardware may include a separate mount structure that is secured to the wall with screws and to which the rear surface of the case body 110 hooks, clips, or is otherwise attached. Various other types of securing hardware for securing the storage case 100 to a structure will be apparent. In various embodiments, the rear surface, bottom surface, or other surface of the case body may include connectors, such as power, network, and phone connections.

The bottom of the case body forms a lower ledge 142 upon which a dispensed medicament 130 rests prior to removal by the user. Before being dispensed, the medicament 130 is retained at another area of the internal area 140 that is inaccessible to the local user or accessible with difficulty. For example, the medicament 130 may be retained at a portion of the internal area 140 that is above the opening and lower ledge 142 and concealed behind the front surface of the storage case 110. In various embodiments, the storage case 100 is configured to store and dispense multiple medicaments, which may be different from each other. For example, in some embodiments, the storage case is able to dispense both adult and child formulations of an epinephrine auto-injector, which may be contained within various packaging such as a product box.

To retain the medicament prior to dispensation, the storage case 100 may include a medicament lock (not shown) or other lockable retaining structure such as a door (not shown). Alternatively, the illustrated door 120 may be lockable in a closed position. Various exemplary medicament locks and other retaining structures will be described below in greater detail. Regardless of the specific retaining structure used, in various embodiments, the retaining structure is electronically movable from a locked state to an unlocked state by an actuator (not shown) controlled by a processor (not shown), which may operate in accordance with received instructions from a remote site to unlock the retaining structure. For example, upon receiving an unlock signal, such as an Internet packet including a dispense instruction, the processor may transmit an access signal to the actuator which, in turn, unlocks the retaining structure. Once the retaining structure is in the unlocked state, the medicament may be free for removal from the device or the user may be able to manually operate the unlocked retaining structure (e.g., open an unlocked door) to free the medicament.

The storage case 100 also includes multiple input/output devices for communicating with the local user. As shown, the storage case includes a "Go" button 111 and a "Stop" button 112. Upon pressing the Go button 111, the storage case 100 may initiate a two-way communication session with a remote site via a communication unit (not shown). The communication session may involve audio communication via a microphone 114 and speaker 115 such that the local user and remote operator may converse. The Stop button 112 may be configured to end the call or otherwise halt any processes performed by the storage case 100 upon a local user pressing the Go button 112.

A display 113 may also be provided for various purposes. For example, the display may facilitate a video feed between the remote site and the local user as part of the two-way communication session and in conjunction with a camera (not shown). Alternatively, the display 113 may show various information to the local user such as medicament usage instructions or status updates regarding the current actions being performed by the storage case 100 or the remote operator. As such, the displayed information may be locally-stored or received from the remote site or elsewhere. In various embodiments, the information displayed on the display 113 is controlled by a remote operator such as a physician. In some embodiments, the display 113 includes a touchscreen input. In such embodiments, the display 113 may include soft buttons instead of or in addition to the Go and Stop buttons 111, 112. A touchscreen display 113 may also be used to provide a management interface accessible via entry of a password, swipe of a keycard, or any other authentication process to provide an authorized user with access to recorded information or to the internal compartment to replace any dispensed or expired medicaments.

Status of the storage case 100 may be communicated in alternative or additional manners. For example, as shown, the storage case 100 includes multiple status lights 116. The status lights may communicate system information, such as power on or boot status, or process flow information, such as whether a call has been placed or whether a medicament has been dispensed. Various other uses for status lights 116 will be apparent.

In various embodiments, the electronics that control the operation of the storage case may be constantly provided with power via a battery, power supply, or other power source. Other embodiments may implement power saving features that reduce energy consumption. For example, during periods of non-use, the electronics of the storage case 100 may be turned off or placed in "sleep" mode. Upon activation by a local user, these electronics may be powered on or awoken to perform the associated functions. For example, opening of the door 120, pressing of the Go button, or pressing of a separate "Power" button may be configured to initiate power on or wake-up of the electronics. Various other power-saving features will be apparent.

Once a medicament has been dispensed, the storage case 100 may be reloaded with additional medicaments by service personnel. While in some embodiments, reloading may be accomplished by opening the case 100, in other embodiments, service personnel may reload the case directly through the front opening product access area without opening the case. Various alternative methods for reloading without requiring special service access (e.g. opening the case) may be utilized such as, for example, loading the medicament through slots in the top of the case, as described below with respect to FIG. 16.

Figure 2:
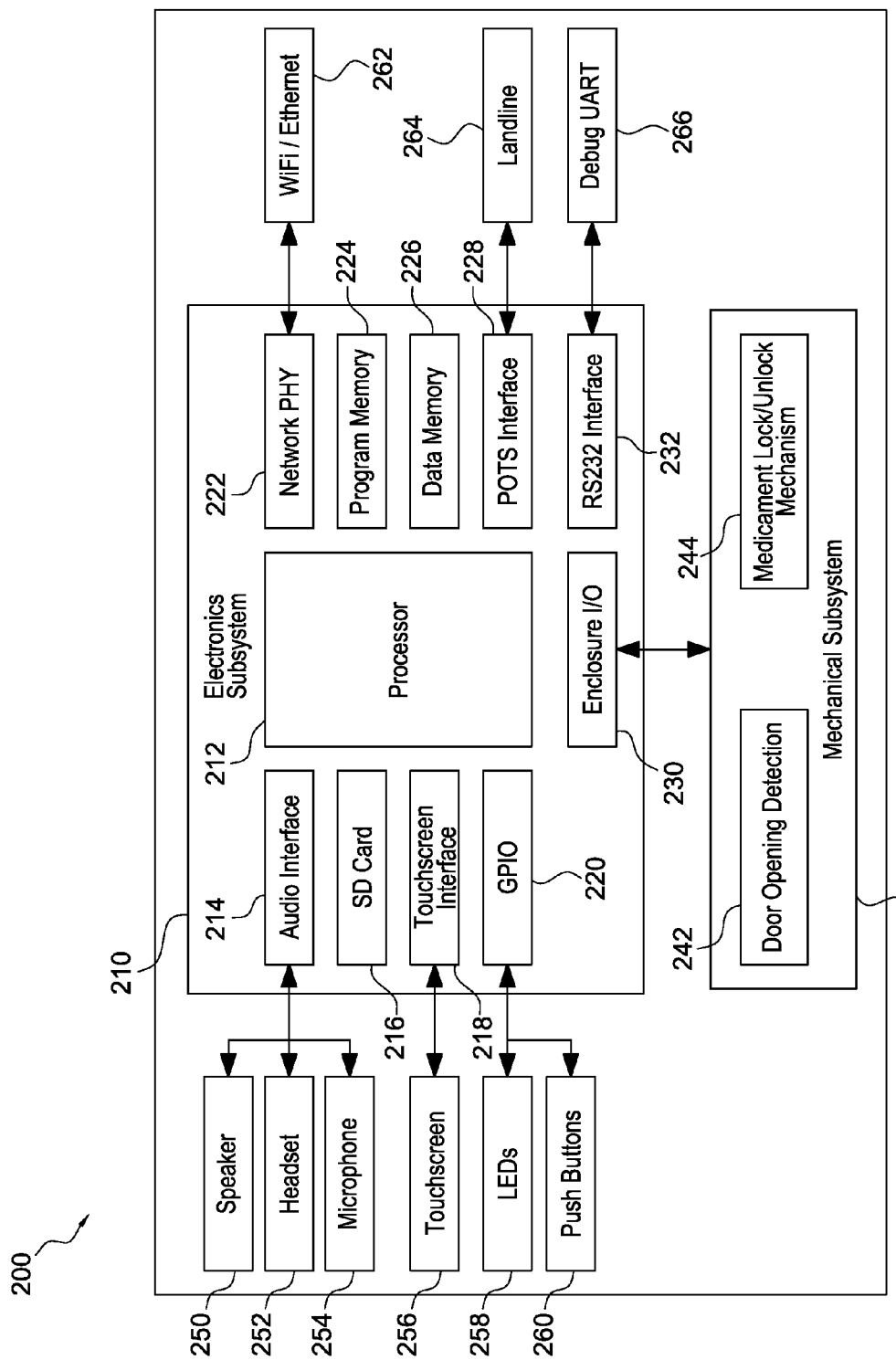
FIG. 2 illustrates a block diagram of exemplary components of a medicament storage case.

FIG. 2 illustrates an exemplary block diagram 200 of exemplary components of a medicament storage case. In various embodiments, the block diagram is representative of the various electronic and mechanical components of the exemplary storage case 100 of FIG. 1.

As shown, the block diagram 200 includes an electronics subsystem 210, a mechanical subsystem 240, and numerous additional components 250-266. The electronics subsystem 210 includes a processor 212 and various supporting electronic components 214-232. The processor 212 may include virtually any device capable of coordinating the functions described herein such as, for example, a microprocessor, a field-programmable gate array (FPGA), or an application-specific integrated circuit (ASIC). In various embodiments, the processor 212 is an ARM architecture microprocessor.

The processor 212 is provided with access to various forms of memory/data storage including an SD card interface 216 and onboard program and data memory 224, 226. The program memory 224 stores software instructions for directing the processor in performing the various methods described herein, such as the exemplary methods described with respect to FIGS. 6-7. For example, the program memory 224 may store an operating system such as a Linux kernel with appropriate device drivers, real-time transport protocol (RTP) stack instructions, session initiation protocol (SIP) stack instructions, direct access arrangement (DAA) stack instructions, and instructions for providing a Qt graphical user interface (GUI). Additionally, the program memory 224 may store event handler instructions for responding to incoming events such as door open/close, watchdog reset, factory reset, firmware upgrade, entry into manufacturing mode, status/reporting, and failure notifications. The program memory 224 may also store various audio components such as advanced Linux sound architecture (ALSA) libraries, software codec instructions, and echo/noise cancellation algorithms.

The data memory 226 may be used by the processor to store various data, such as log data regarding usage of the storage case, location information, or a log of temperature information. Various other data for storage in the data memory 226 or on an SD or other memory card will be apparent in view of the present description. Alternatively or additionally, an SD or other memory card 216 may be used to store boot-up instructions, firmware images, activity logs, predefined information and messages, and other information.

The electronics subsystem 212 includes an audio interface 214, such as an audio codec, for enabling the processor to receive and output audio via various audio devices such as a speaker 250, a headset 252, or a microphone 254. Similarly, the electronics subsystem 210 includes a touchscreen interface 218 for outputting visual data to and receiving touch input from a touchscreen device 256. For various other input/output devices, such as status LEDs 258 or push-buttons 260, the electronics subsystem 210 provides a general purpose input/output (GPIO) interface 220.

The processor 212 may also have access to various external devices. For example, to connect to other devices via the Internet or other network, the electronics subsystem 210 includes a physical network interface (PHY) which communicates via various media such as Ethernet or WiFi 262. Additionally, the electronics subsystem 210 includes a plain ordinary telephone system (POTS) interface 228 to enable establishment of phone calls via a landline 264. To enable system debugging and other maintenance, the electronics subsystem 210 includes an RS-232 serial interface 232 to which a device with a universal asynchronous receiver/transmitter (UART) may be attached to exchange data and instructions with the processor.

The electronics subsystem 210 may also include an enclosure I/O interface 230 for communicating with the mechanical subsystem 240. In various embodiments, the enclosure I/O interface 230 may simply utilize the GPIO interface 220. The mechanical subsystem 240 includes two devices. A door opening detection device, such as a switch, button, proximity sensor, or motion detector, may be positioned to send a signal to the enclosure I/O interface 230 when the door is opened. In various embodiments, this signal may be used to power on or wake up the electronics subsystem 210. A medicament lock/unlock mechanism 244 such as a solenoid interface or other actuator interface receives access signals from the processor 212 via the enclosure I/O interface 244. Upon receiving such as signal, the medicament lock/unlock mechanism 244 causes a medicament to be dispensed, as will be explained in greater detail below.

Figure 3:
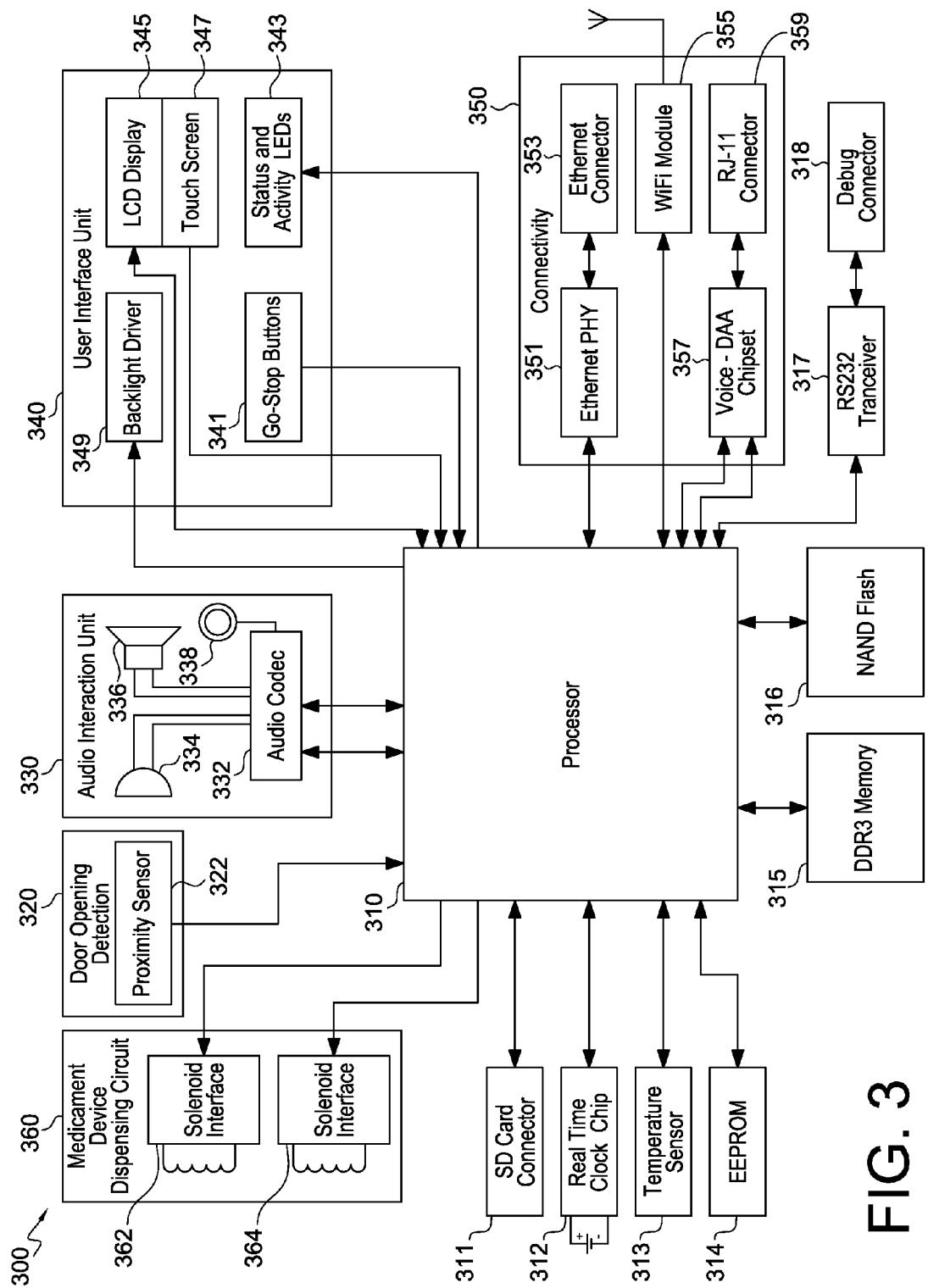
FIG. 3 illustrates an exemplary schematic diagram of exemplary components of a medicament storage case.

FIG. 3 illustrates an exemplary schematic diagram 300 of exemplary components of a medicament storage case. In various embodiments, the schematic diagram 300 may describe the various systems of the exemplary storage case 100 and may illustrate a more detailed embodiment of the block diagram 200 of FIG. 2.

As shown, the system is arranged around a processor 310 which, as described above, may be a microprocessor, FPGA, ASIC, or any other device capable of performing the functions described. The processor 310 may include some onboard memory and may additionally have access to other forms of memory such as an SD card connector 311, and EEPROM 314, a DDR3 memory 315, and a NAND flash memory 316. The processor 310 may communicate with the SD card connector 311 via a secure digital input output (SDIO) bus. Various data and instructions may be stored among these memory devices. Further, it will be apparent that fewer or additional memory devices, and memory devices of different types from those shown, may be utilized.

The processor may also make use of other devices that do not belong to an otherwise-described subsystem. For example, in various embodiments, the system 300 may keep a log of usage based on a date and time reported by a real time clock chip 312. In some embodiments, the processor 310 may log or monitor a temperature of the medicaments or the surrounding area, as reported by a temperature sensor 313. In some embodiments, the temperature sensor 313 may be used by the processor 310 or other chip (not shown) to regulate the temperature to which the medicaments are exposed. For example, a storage case may be provided with fans or other devices for controlling an internal temperature. The processor 310 may be configured in such embodiments to control the fans in response to the temperature sensor 313 reporting a temperature or time-temperature reading that is higher than some predetermined threshold. Such features may be particularly useful in embodiments where the storage case is portable or may otherwise be subjected to inconsistent climates. Further, as described above, the processor 310 may provide a debug or maintenance interface to other devices via a RS232 transceiver 317 and connector 318.

As explained, in various embodiments, the system 300 may be powered on or awoken in response to detecting that the door has been opened. To provide such functionality, a door opening detection module 320 including one or more proximity sensors 322 for detecting that the door has been moved away from the closed position. Such information may be transmitted to the processor via one or more GPIO lines. In various alternative embodiments, the proximity sensor 322 may be replaced with other devices such as a dedicated power button or one of the go-stop buttons 341.

To facilitate audio communication, an audio interaction unit 330 is in communication with the processor 330. Namely, the audio interaction unit 330 includes an audio codec 332 that exchanges data with the processor 310 via a multichannel audio serial port (McASP) and an inter-integrated circuit (I2C) bus. The audio codec 332, in turn, renders audio data received from the processor 310 through a headset 334 and speaker 336 and digitizes analog audio data received via a microphone 338. As will be understood, the processor may simply act as a passthrough for such audio data, enabling exchange of the data between the audio interaction unit and a connectivity unit 350. In other embodiments, the audio interaction unit 330 may be connected directly to the connectivity unity 350 thereby allowing data to be transferred with a remote location without the processor 310 handling such data. For example, the audio interaction unit 330 may transmit and receive analog audio data via the RJ-11 connector. In some embodiments, such a direct connection may be selectively enabled or disabled by the processor 310.

For additional types of local user interaction, the system 300 includes a user interface unit 340 including various input and output devices. For example, the user interface unit 340 may include Go and Stop buttons 341 that may be used to initiate and interrupt operation of the system to connect to a remote site. As such, the Go and Stop buttons 341 may provide signals to the processor 310 via one or more GPIO channels. Similarly, the processor may be configured to illuminate status and activity LEDs 343 by transmitting signals via one or more GPIO channels.

The user interface unit 340 also includes an LCD display 345 and integrated touch screen 357. The processor 310 may output visual data, such as predefined instructions stored among the memory devices 311, 314, 315, 316 or information received via the connectivity module 350, to the LCD display 345 via a display interface. The processor 310 also receives any input received by the touch screen 347 through the touch screen interface. Various embodiments may also facilitate usage of the system in low-light conditions by providing a backlight driver 349 for controlling backlighting to the LCD display 345, Go-Stop buttons 341, or other components. The processor may transmit an indication of the intensity of the backlighting desired to the backlight driver 349 via a pulse-width modulation channel.

The processor 310 is provided with the ability to communicate with remote devices via the connectivity module 350. As shown, the connectivity module 350 provides three channels of communication. It will be appreciated that fewer or additional communication channels may be supported. As a first channel, the connectivity module includes an Ethernet PHY chip 351 that enables wired network communication via an Ethernet connector 353, such as an RJ-45 connection. The processor 310 may transfer data to and from the Ethernet PHY chip via a media independent interface (MII). To provide a second network channel, the connectivity module 350 includes a WiFi module 355 which includes an antenna and the WiFi PHY chip. The processor 310 may transfer data to and from the WiFi module 355 via a SDIO bus. The third channel provided by the connectivity module 350 is a landline POTS connection. As such, the connectivity module 350 includes a voice direct access arrangement (DAA) chipset 357 in communication with the phone line via an RJ-11 connector 359. The processor 310 may be in communication with the voice DAA chipset 357 via an SPI bus and a McASP.

To effect release of medicaments, the processor 310 is in communication with a medicament device dispensing circuit 360. Specifically, the processor 310 may be in communication with one or more solenoid interfaces 362, 364 or other interfaces for effecting dispensing of a medicament. In various embodiments, the processor 310 communicates with each of the solenoid interfaces 362, 364 via a general purpose 10 channel, respectively.

In some embodiments, various electronic circuits may include self-diagnostic or feedback capabilities. For example, the self-diagnostic or feedback methods may be employed to monitor the state of the solenoid loop, to monitor battery degradation, or to monitor other key functionalities. Methods for implementing such capabilities will be apparent.

It will be appreciated that some devices that may be used in implementing the exemplary system 300 may be omitted. For example, in implementations of the system, a telephone line translator may be positioned between the voice DAA chipset 357 and the RJ-11 connector or magnetic may be provided between the Ethernet PHY chip 351 and the Ethernet connector 353. Further, additional lines of communication may be provided between the various chips. For example, the processor 310 may additionally transmit various signals in addition to the display data to the LCD display 345 such as an enable or read/write signal. Various additional implementation details that have been omitted will be apparent.

Figure 4:
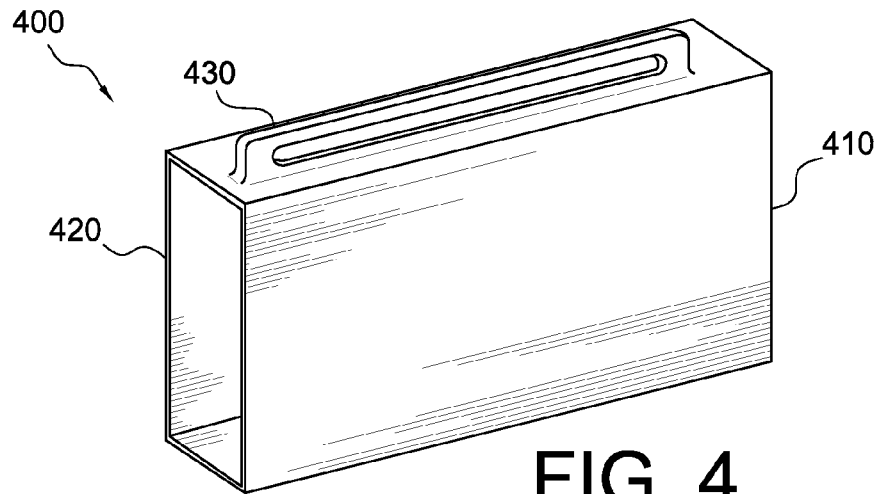
FIG. 4 illustrates an exemplary sleeve for containing a medicament.

As noted, medicaments may be dispensed with or without packaging. In some embodiments, retention and release of the medicaments may be facilitated by a separate sleeve, case, or other apparatus that contains or holds the medicament and provides other structural features for engagement with the medicament lock or other retaining structure of the storage case. FIG. 4 illustrates an exemplary sleeve 400 for containing a medicament. The sleeve 400 may be made of virtually any material; in some embodiments, the sleeve 400 is formed of acrylonitrile butadiene styrene (ABS) plastic or other material that is sufficiently strong to withstand or absorb drop forces to preserve the integrity of any medicaments housed inside the sleeve 400. The sleeve includes a hollow sleeve body 410, at least one opening 420 near at least one end, and a rail 430 extending from an upper surface of the body 410. The opening is sized to receive a box packaging for a medicament. For example, a standard commercial box packaging including two epinephrine pens may be inserted through the opening 420 and received within the body 410. The rail 430 is provided to engage the medicament lock or other retaining structure of the storage case, an example of which will be described below with respect to FIG. 5.

It will be apparent that the sleeve 400 is one example and that various alternative structures may be used. For example, the sleeve may not include an opening 420 and, instead, may include a hinged engagement between two portions of the body such that the sleeve may be opened. As another example, the rail 430 may be replaced with a round loop, magnet, or other structure or material suitable for engaging the particular retaining structure used. Further, the body 410 may be formed in a different shape. For example, where the medicament is dispensed without packaging, the body 410 may instead be a round sleeve or other shape structured to contain the medicament. In some embodiments, the body 410 may be omitted and the rails 430 or other engaging structure may be attached directly to the medicament or medicament packaging via adhesive, screws, or other attachment means or may be integrally formed with the medicament or packaging. Various additional modifications will be apparent.

Figure 5:
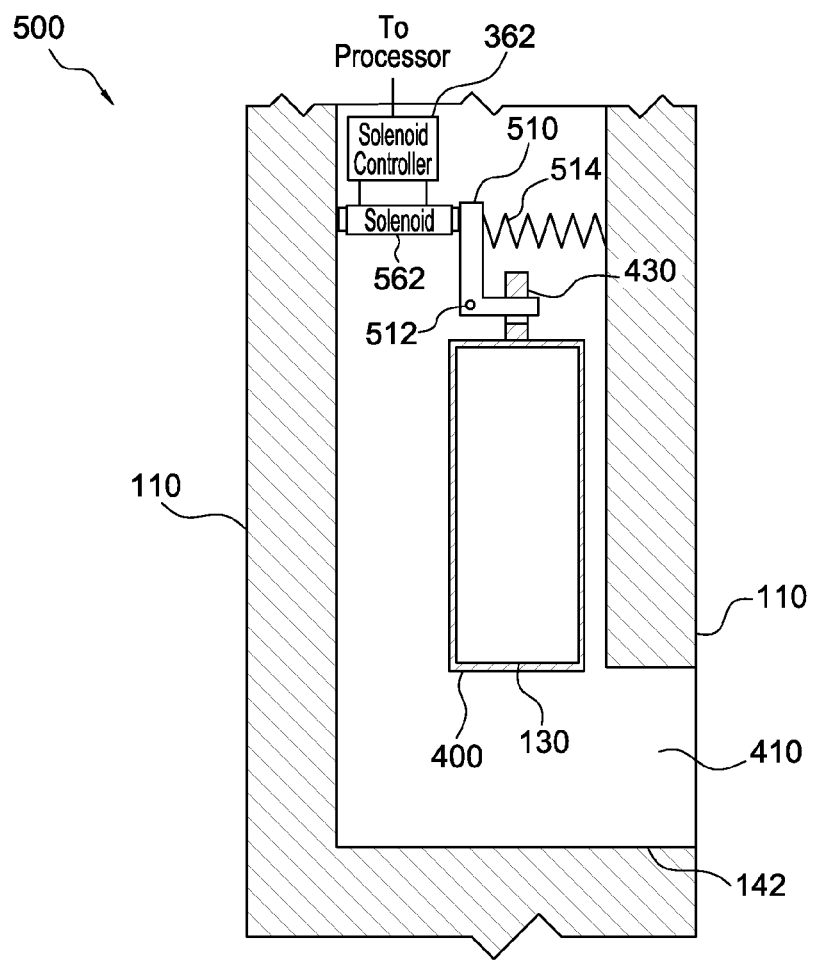
FIG. 5 illustrates a cross section of an exemplary medicament storage case, including an exemplary actuator for selectively retaining and releasing a sleeve.

FIG. 5 illustrates a cross section 500 of the exemplary medicament storage case 110 of FIG. 1 as viewed from the side, including an exemplary actuator for selectively retaining and releasing a sleeve. The case body 110 provides front and rear surfaces forming the internal area 140 therebetween.

The sleeve 400, containing the medicament 130, is suspended within the internal area 140 by the sleeve rail 430. As shown, a hook 510 is received under the rail 430 such that the sleeve 400 hangs from the hook 510. The hook 510 is held in place at a pivot point 512. For example, a rod, pin, or other structure may be inserted through the hook 510 at the pivot point 512 which allows the hook to rotate clockwise or counter clockwise as viewed from the perspective of FIG. 5. The weight of the sleeve 400 and medicament 130 tends to force the hook to rotate clockwise; as may be seen, upon the hook 510 rotating sufficiently far clockwise, the rail 430 would slide off of the hook 510. No longer supported by the hook 510, the sleeve 400 would fall and land on the lower ledge for retrieval by the user. To counteract the downward force of the sleeve 400 on the hook 510, a spring of sufficient strength is disposed between the top portion of the hook 510 and the case body 110. As such, when no other outside forces act upon the hook 510, the hook retains the sleeve 400 in suspension.

To effect release of the retaining structure (e.g., the hook 510 and spring 514), an actuator including a solenoid 562 and solenoid controller 362 are provided. As described above, the solenoid controller 362 receives an access signal from the processor and, in response, sends a current through the solenoid 562 sufficient to move the solenoid cylinder forward (to the right from the perspective of FIG. 5) and impose a third force on the hook 512. The force of the solenoid 562 together with the downward force of the sleeve 400 and medicament 130 are sufficiently high to counteract the force of the spring 514 and thereby cause the hook 510 to rotate and release the sleeve 400.

It will be apparent that the arrangement of FIG. 5 is but one example of a retaining structure and actuator for dispensing a medicament and that numerous additional configurations are possible. For example, the sleeve 400 may be suspended directly from the solenoid cylinder, which is moved out of engagement with the sleeve 400 upon activation by the solenoid controller 362. In such an embodiment, the components of the solenoid 562 may serve as both the retaining structure and the actuator. Similarly, in some embodiments, the solenoid cylinder may be in contact with or formed with another non-pivoting structure that is moved linearly out of engagement with the sleeve 400. As another alternative, instead of suspending the sleeve 400 or the medicament 130, the sleeve 400 or the medicament 130 along may rest on a movable platform. Upon activation, the platform may retract or pivot, such that the sleeve 400 or medicament 130 is no longer supported and falls to the lower ledge 142.

It will also be appreciated that various arrangements may use actuators other than solenoids. For example, a servo motor or stepper motor may be used to control the angular position of the hook 510 or a platform or may be used to linearly retract another retaining structure via one or more linkage structures (e.g., by winding a cable attached to the structure). As another example, where the retaining structure is an electromagnet, the actuator may be a controller adapted to cut power to the magnet, thereby releasing the sleeve 400 or medicament 130. Various other types of actuators will be apparent.

Further various other retaining structures and actuator arrangements may be utilized that do not deliver the medicament through dropping the medicament to a user accessible area. For example, a medicament 130 may be locked to the storage case by a ring or clamp disposed around the medicament 130 and that may be opened by an appropriate actuator. As another example, the medicament 130 may be stored behind a locked door (e.g., a secondary door behind the primary door 120, or behind the primary door 120 in an embodiment where the controls such as the Go button 111 are not also housed behind the primary door) or within a locked drawer. The actuator in such embodiments may serve to unlock such a door or drawer, allowing the user to open the door or drawer and gain access to the medicament. Thus, in some embodiments the actuator effects active release of the medicament 130, such that the user may directly retrieve the medicament 130 after release, while in other embodiments the actuator effects passive release of the medicament 130, such that the user is able to manually move the retaining structure to gain access to the medicament 130.

Figure 6:
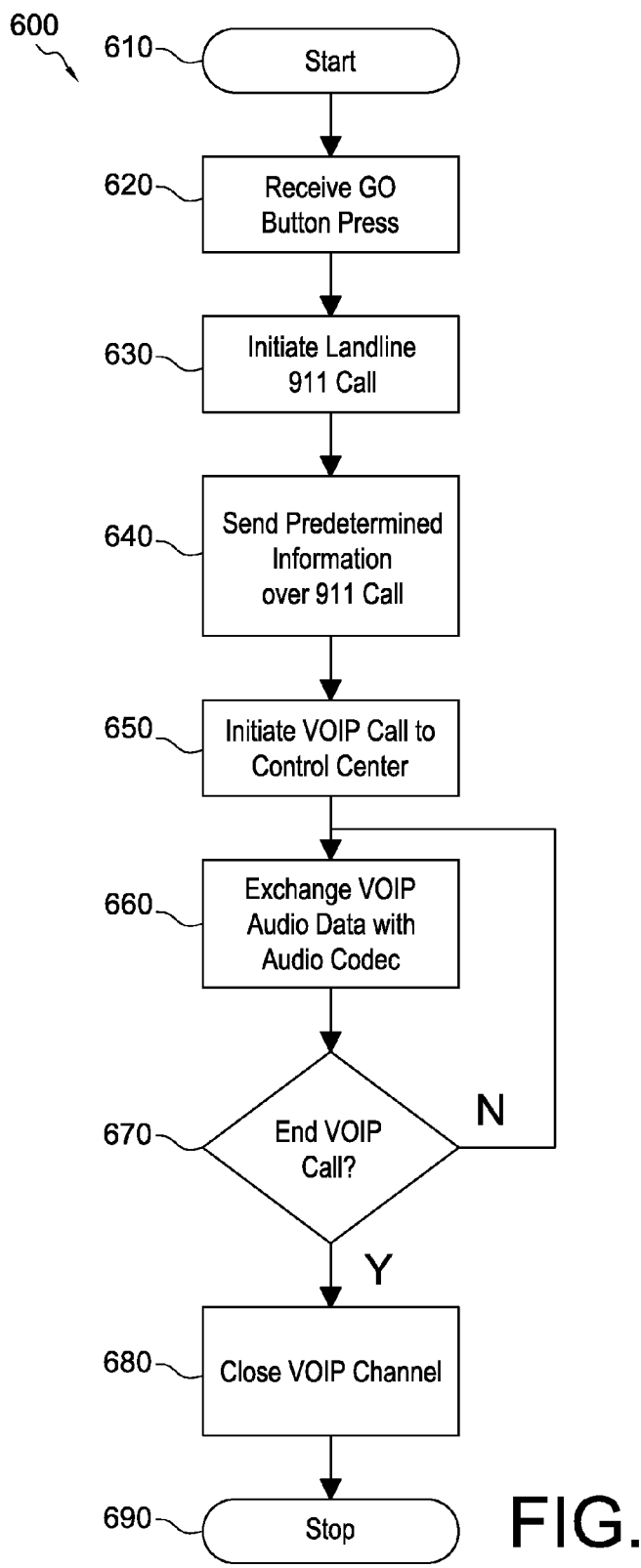
FIG. 6 illustrates an exemplary method for contacting emergency services via a medicament storage case.

FIG. 6 illustrates an exemplary method 600 for contacting emergency services via a medicament storage case. The method 600 may be performed by a processor of the storage case 100, such as processor 212 or processor 310, and may be encoded as program instructions for execution by such a processor.

The method 600 begins in step 610 and proceeds to step 620 where the processor receives an indication that the Go button has been pressed. Such button press may be detected via a physical Go button such as button 111 or via a soft Go button such as may be displayed on a touchscreen display such as display 113. In various embodiments, the step 620 consists of the processor receiving and recognizing an event at an event handler.

Next, in step 630, the processor initiates a landline call to an emergency dispatch. For example, where the storage case is located in the U.S., the processor may be configured to place a phone call to 911 emergency services. During or after connection to the emergency dispatch, the processor transmits a set of predetermined information to the emergency dispatch via the landline call. For example, the processor may transmit an indication that the call is from a medicament storage case, that no voice session is being established with the local user, or a location of the storage case which may be pre-programmed or determined at the time of the via GPS or other means. Various additional or alternative information to transmit to the emergency dispatch will be apparent. The information may be transmitted in any form such as, for example, computer-rendered voice audio, fax data, or data otherwise encoded on an analog telephone signal.

Next, in step 650, the processor initiates a voice-over-IP (VOIP) call to a control center other than the emergency dispatch. For example, the control center may be operated by the same entity that provides, maintains, or is otherwise associated with the storage case or the medicament contained therein. Again, the storage case may also transmit various predefined information, such as the location or an identifier of the storage case. Then, in step 660, the processor exchanges audio data between the audio codec and the VOIP channel, such that the local user is able to converse with the operator at the control center. As will be described below, the control center operator may transfer the call to a physician, after which the local user may converse with the physician. In step 670, the processor determines whether to end the VOIP call. For example, the processor may determine whether the Stop button has been pressed or if the VOIP call has been closed from the other end. If not, the method 600 loops back to step 660 to continue to exchange audio data with the remote site. Otherwise, the processor proceeds to close the VOIP channel in step 680 and the method ends in step 690.

It will be appreciated that the method 600 is one example of the operation of a medicament storage case in accordance with the systems and methods described herein and that various alternative methods may be used. For example, step 670 may be accomplished through the event handler and detection of the events that would close the call. In some embodiments, no call to the emergency dispatch may be placed, while in other embodiments only the call to 911 may be placed where the emergency dispatch is equipped to remotely control dispensation of the medicament or to transfer the call to a physician or other entity so-equipped. In other embodiments, various steps of the method are performed in parallel. For example, step 620 may split into two threads: a first thread with steps 630, 640 and a second thread with steps 650-680. In such embodiments, the two calls may be placed simultaneously. Various other modifications will be apparent.

Figure 7:
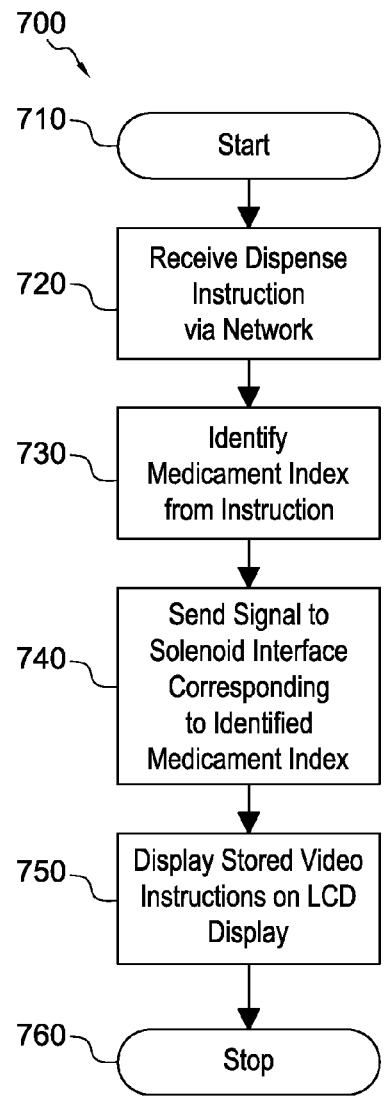
FIG. 7 illustrates an exemplary method for allowing access to a medicament in response to a remote instruction.

FIG. 7 illustrates an exemplary method 700 for allowing access to a medicament in response to a remote instruction. The method 700 may be performed by a processor of the storage case 100, such as processor 212 or processor 310, and may be encoded as program instructions for execution by such a processor.

The method begins in step 710 and proceeds to step 720 where the processor receives an unlock signal that serves as a dispense instruction. For example, the processor may receive a packet including an instruction to dispense a medicament. In step 730, the processor determines, from the instruction, the index of the medicament to be dispensed. In particular, in embodiments where the storage case is capable of dispensing multiple different medicaments and dosages, the available medicaments may be indexed. For example, an adult epinephrine injector set may be indexed "0" while a child epinephrine injector set may be indexed "1." The instruction received in step 720 may directly specify the index to the appropriate medicament or may only specify the medicament to be dispensed, in which case the processor determines the index of the identified medicament through, for example, a lookup table. In embodiments where only a single type of medicament may be dispensed, the step 730 may be omitted.

In step 740, the processor sends an access signal to the actuator associated with the appropriate medicament. Again, this step may include correlating an index or medicament to an actuator through, for example, a lookup table. Upon receiving the access signal, the actuator releases the medicament for retrieval by the user. In various alternative embodiments, a single actuator may control the release of multiple medicaments; in such embodiments, the processor may simply send the index or other identification of the desired medicament to the actuator which, in turn, determines the appropriate action to dispense the requested medicament.

After dispensing the medicament, the processor locates stored video instructions for the medicament or receives such instructions via the network interface. In step 750, the processor outputs the instructions via the display device, thereby reinforcing any physician or other remote operator instructions with visuals. The method 700 then proceeds to end in step 760.

Figure 8:
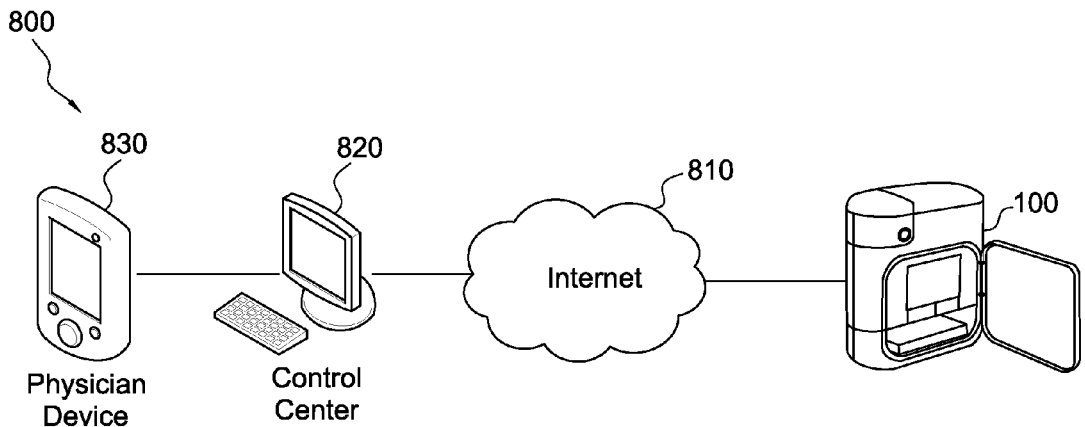
FIG. 8 illustrates an exemplary network environment for a medicament storage case.

FIG. 8 illustrates an exemplary network environment 800 for a medicament storage case. As explained in detail above, the operations of the storage case 100 are at least partially controlled by remote devices such as a control center device 820 or a physician device 830 via the Internet 810 or other network. The control center device 820 or physician device 830 may be virtually any user device such as a terminal, personal computer, tablet, mobile phone, or other device.

As explained, upon activation by a user, the storage case 100 initiates a VOIP call to a remote site such as the control center 820 or an emergency dispatch (not shown). The control center 820, either immediately or at some time during the call may transfer the VOIP call to a physician who is either on-site or on-call. In some embodiments, the control center 820 may simply operate as an electronic dispatch that automatically forwards the call to an available physician device 830. In such embodiments, the control center 820 may be hosted within a cloud computing environment.

The control center 820 or physician device 830, in addition to facilitating the audio VOIP call, may also provide the remote operator the ability to remotely release one or more medicaments at the storage case 100. For example, the physician device 830 may run a mobile app that both communicates audio data between the physician and the storage case and presents two buttons to the physician: a button to dispense an adult formulation epinephrine injector and a button to dispense a child formulation epinephrine injector. Such buttons may result in the physician device generating and transmitting a release signal, such as a dispense instruction packet, to the storage case 100 either via the control center 820 or directly through the Internet 810 bypassing the control center 820. Similar functionality may be provided at the control center 820.

Various modifications and additional features will be apparent. For example, the control center 820 or physician device 830 may be further configured to support a one- or two-way video feed with the storage case 100. As another alternative, the control center 820 or physician device 830 may enable the remote operator to select or transmit text or graphics to be displayed on a display device of the storage case 100. Further the control center 820 or physician device 830 may interface with other devices (not shown) such as a patient record repository such that the remote operator is able to access a medical history of the patient.

In some embodiments, a management system may also be in communication with the storage case 100 via the Internet 810 or other network. For example, a separate server, personal computer, table, laptop, cloud virtual machine, or the control center 820 itself may communicate with the storage case to perform functions such as inventory management, call recording & logging, and other management functions.

Figure 9:
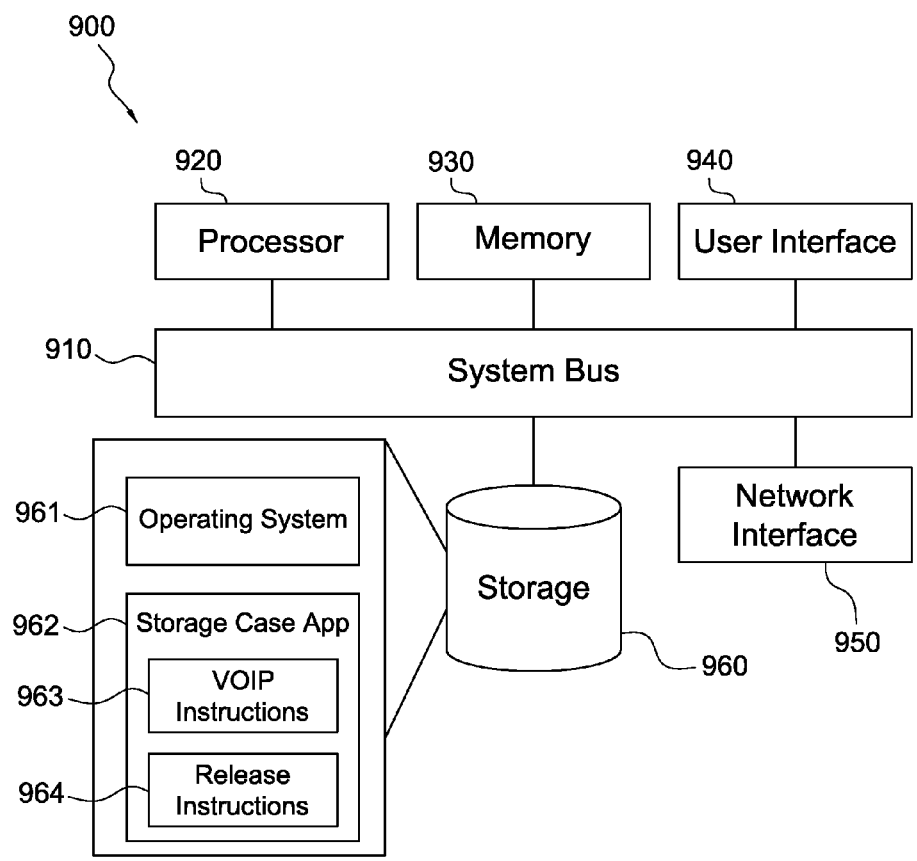
FIG. 9 illustrates an exemplary hardware diagram for a physician device or control center device.

FIG. 9 illustrates an exemplary hardware diagram 900 for a physician device or control center device. In various embodiments, exemplary hardware diagram 900 may also describe at least a portion of the storage case. As shown, the hardware 200 includes a processor 920, memory 930, user interface 940, network interface 950, and storage 960 interconnected via one or more system buses 910. It will be understood that FIG. 9 constitutes, in some respects, an abstraction and that the actual organization of the components of the hardware 900 may be more complex than illustrated.

The processor 920 may be any hardware device capable of executing instructions stored in memory 930 or storage 960 or otherwise processing data. As such, the processor 920 may include a microprocessor, field programmable gate array (FPGA), application-specific integrated circuit (ASIC), or other similar devices.

The memory 930 may include various memories such as, for example L1, L2, or L3 cache or system memory. As such, the memory 930 may include static random access memory (SRAM), dynamic RAM (DRAM), flash memory, read only memory (ROM), or other similar memory devices.

The user interface 940 may include one or more devices for enabling communication with a user such as an administrator. For example, the user interface 940 may include a display, a mouse, and a keyboard for receiving user commands. In some embodiments, the user interface 240 may include a command line interface or graphical user interface that may be presented to a remote terminal via the network interface 950.

The network interface 950 may include one or more devices for enabling communication with other hardware devices. For example, the network interface 950 may include a network interface card (NIC) configured to communicate according to the Ethernet protocol. Additionally, the network interface 950 may implement a TCP/IP stack for communication according to the TCP/IP protocols. Various alternative or additional hardware or configurations for the network interface 950 will be apparent.

The storage 960 may include one or more machine-readable storage media such as read-only memory (ROM), random-access memory (RAM), magnetic disk storage media, optical storage media, flash-memory devices, or similar storage media. In various embodiments, the storage 960 may store instructions for execution by the processor 920 or data upon with the processor 920 may operate. For example, the storage 960 may store a base operating system (OS) 961 such as Linux, MICROSOFT WINDOWS OS, APPLE OS X, APPLE iOS, or GOOGLE ANDROID OS. The storage 960 also includes instructions for defining an application 962 that communicates with one or more storage cases. As part of the storage case app 962, the storage 960 may store VOIP instructions 963 for communicating audio or video data with the storage case and release instructions 964 for instructing, at the command of the user of the hardware 900, the storage case to release a medicament.

It will be apparent that various information described as stored in the storage 960 may be additionally or alternatively stored in the memory 930. For example, the operating system 961 and wall unit app 962 may be copied, at least partially, to memory 930 for execution by the processor 920. In this respect, the memory 930 may also be considered to constitute a "storage device" and the storage 960 may be considered a "memory." Various other arrangements will be apparent. Further, the memory 930 and storage 960 may both be considered to be "non-transitory machine-readable media." As used herein, the term "non-transitory" will be understood to exclude transitory signals but to include all forms of storage, including both volatile and non-volatile memories.

While the hardware 900 is shown as including one of each described component, the various components may be duplicated in various embodiments. For example, the processor 920 may include multiple microprocessors that are configured to independently execute the methods described herein or are configured to perform steps or subroutines of the methods described herein such that the multiple processors cooperate to achieve the functionality described herein.

Having described one exemplary embodiment of a medicament storage case with respect to FIGS. 1-9, various alternative embodiments will now be described. It will be understood that the various features disclosed among all embodiments described herein may be combined to yield further alternative embodiments within the scope of the methods and techniques described herein.

FIG. 10 illustrates a first alternative embodiment of a medicament storage case 1000. As shown, the first alternative embodiment 1000 is similar to the embodiment of FIG. 1, including a storage case body 1010, hinged door 120, Go button 111, Stop button 112, display device 113, and dispensable medicament 130. The first alternative embodiment 1000 also includes a detachable communications unit 1040 that includes a camera 1042. Alternatively or additionally, the detachable communications unit 1040 may include a speaker or a microphone. The detachable communications unit 1040 may be removed from the case body 1010 and transported to another location, such as a location of a patient that may not be near the storage case body 1010. The detachable communications unit 1040 may relay visual or audio data to and from the storage case 1000 via a wireless communications medium such as, for example, a WiFi or Bluetooth connection. As such, the remote operator, such as a physician, may be able to visualize or communicate with a patient that is unable to walk to the wall-mounted storage case 1000.

In various embodiments, the detachable communications unit 1040 may be freely detachable by a user while, in other embodiments, removal of the detachable communications unit 1040 may be restricted. For example, the detachable communications unit 1040 may only be removable once a call to the control center has been place or upon receipt of an instruction from the control center or physician to release the detachable communications unit 1040. Selective release of the detachable communications unit 1040 may be provided in virtually any of the manners described herein with respect to providing selective access to medicaments. For example, the detachable communications unit 1040 may be secured to the body 1010 via one or more movable tabs or hooks. Upon receipt of an instruction to release the detachable communications unit 1040, the processor may then signal one or more solenoid controllers to activate one or more solenoids arranged to disengage the tabs or hooks, thereby release the detachable communications unit 1040.

FIG. 11 illustrates a cross-section 1100 of the first alternative embodiment of a medicament storage case. The cross-section 1110 shows that, instead of suspending a medicament for dispensing, the medicaments 130, 131 may rest on respective platforms or doors 1150, 1151. Upon activation by the electronics 1117, an actuator such as a solenoid, servo motor, or stepper motor may slide or rotate one of the platforms 1150, 1151 such that the associated medicament 130, 131 is no longer supported and slides down the curved back wall toward the front opening.

Figure 12:
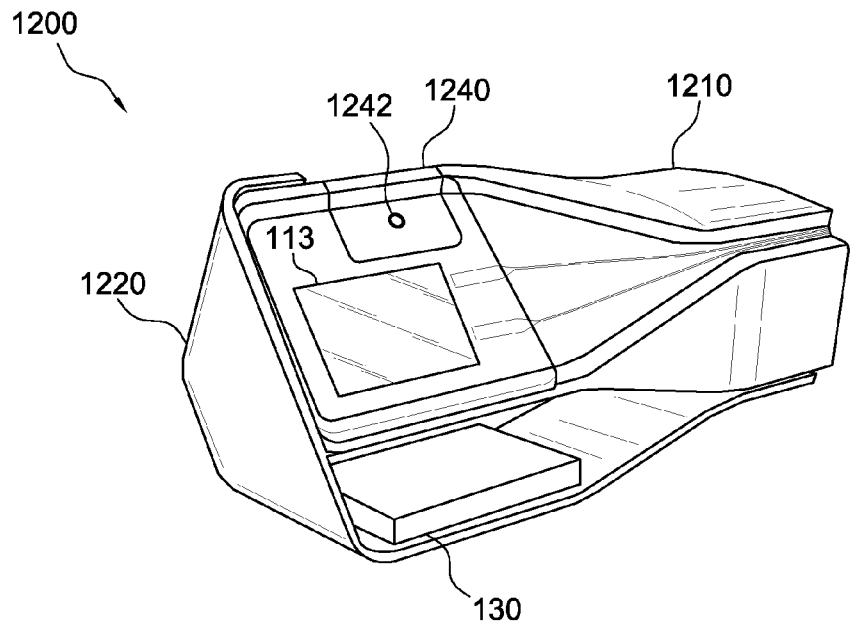
FIG. 12 illustrates a second alternative embodiment of a medicament storage case.

FIG. 12 illustrates a second alternative embodiment of a medicament storage case 1200. The second alternative embodiment 1200 includes a case body 1210 and a separate shell 1220 that forms a ledge for the dispensed medicament 130. The second alternative embodiment 1200 also includes a touchscreen display device 113 and a detachable communications unit 1240 including a camera 1242. The second alternative embodiment 1200 lacks physical buttons and, instead, may provide only software buttons via the touchscreen display device 113.

Figure 13:
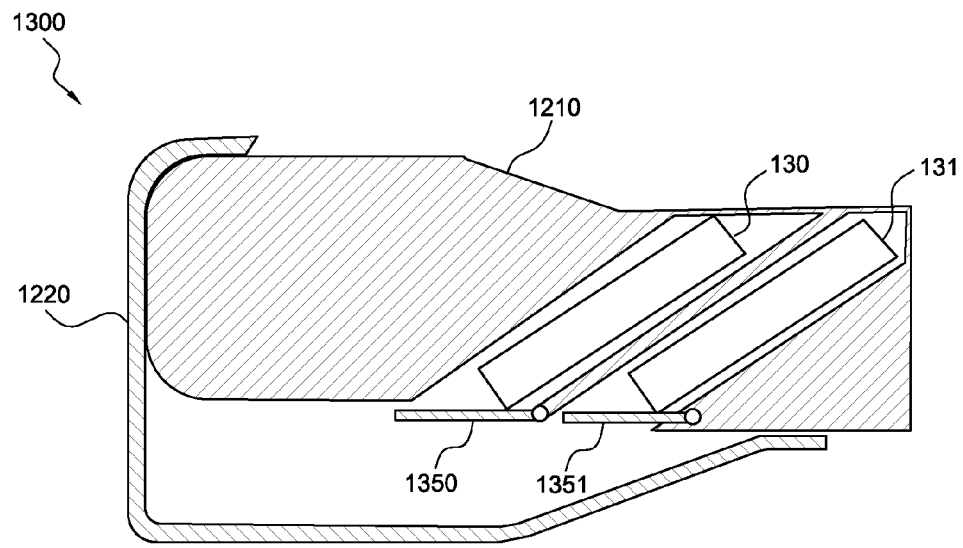
FIG. 13 illustrates a cross-section of the second alternative embodiment of a medicament storage case.

FIG. 13 illustrates a cross-section 1300 of the second alternative embodiment of a medicament storage case. As shown, the case body 1210 forms two recesses for receiving medicaments 130, 131. The recesses are associated with respective doors 1350, 1351 that may be actuated by the electronics to release medicaments 130, 131 to slide down to the lower ledge formed by the shell 1220.

Figure 14:
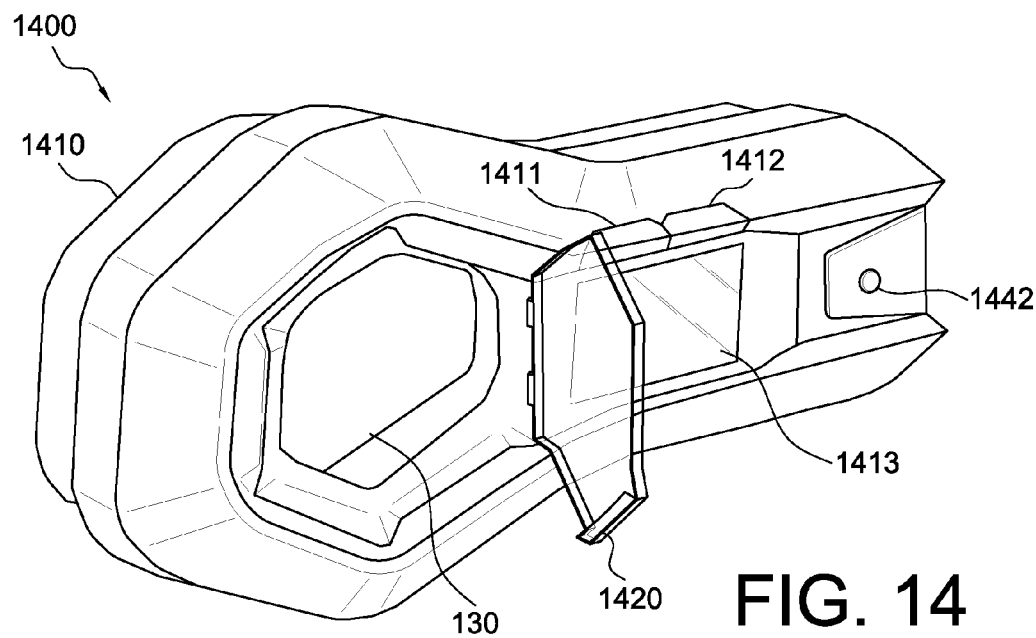
FIG. 14 illustrates a third alternative embodiment of a medicament storage case.

FIG. 14 illustrates a third alternative embodiment of a medicament storage case 1400. The third alternative embodiment 1400 includes a case body 1410, a Go button 1411, a Stop button 1412, a display device 1413, and a camera 1442 which may be part of a detachable communications unit. Additionally, the third alternative embodiment 1400 includes a door 1420 that, when closed, blocks access to the medicament 130. Upon actuation by the electronics, the door 1420 may become unlocked, such that the local user may manually open the door and remove the medicament from the interior area.

Figure 15:
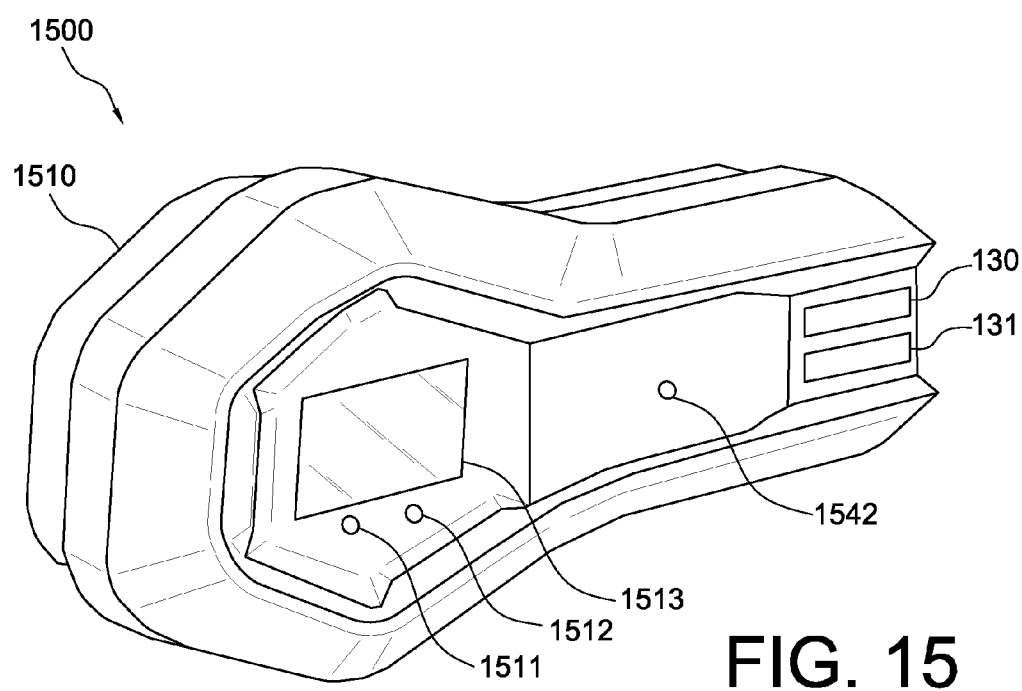
FIG. 15 illustrates a fourth alternative embodiment of a medicament storage case.

FIG. 15 illustrates a fourth alternative embodiment of a medicament storage case 1500. The fourth alternative embodiment 1500 is similar to the third alternative embodiment 1400 but includes components in different locations. As shown, the fourth alternative embodiment 1500 includes a body 1510, a Go button 1511, a Stop button 1512, a display device 1513, a camera 1542, and two medicaments 130, 131 disposed within respective locked drawers. Upon actuation by the electronics, one of the drawers may become unlocked, such that the user may pull the drawer and respective medicament 130, 131 out of the side of the body 1510

Figure 16:
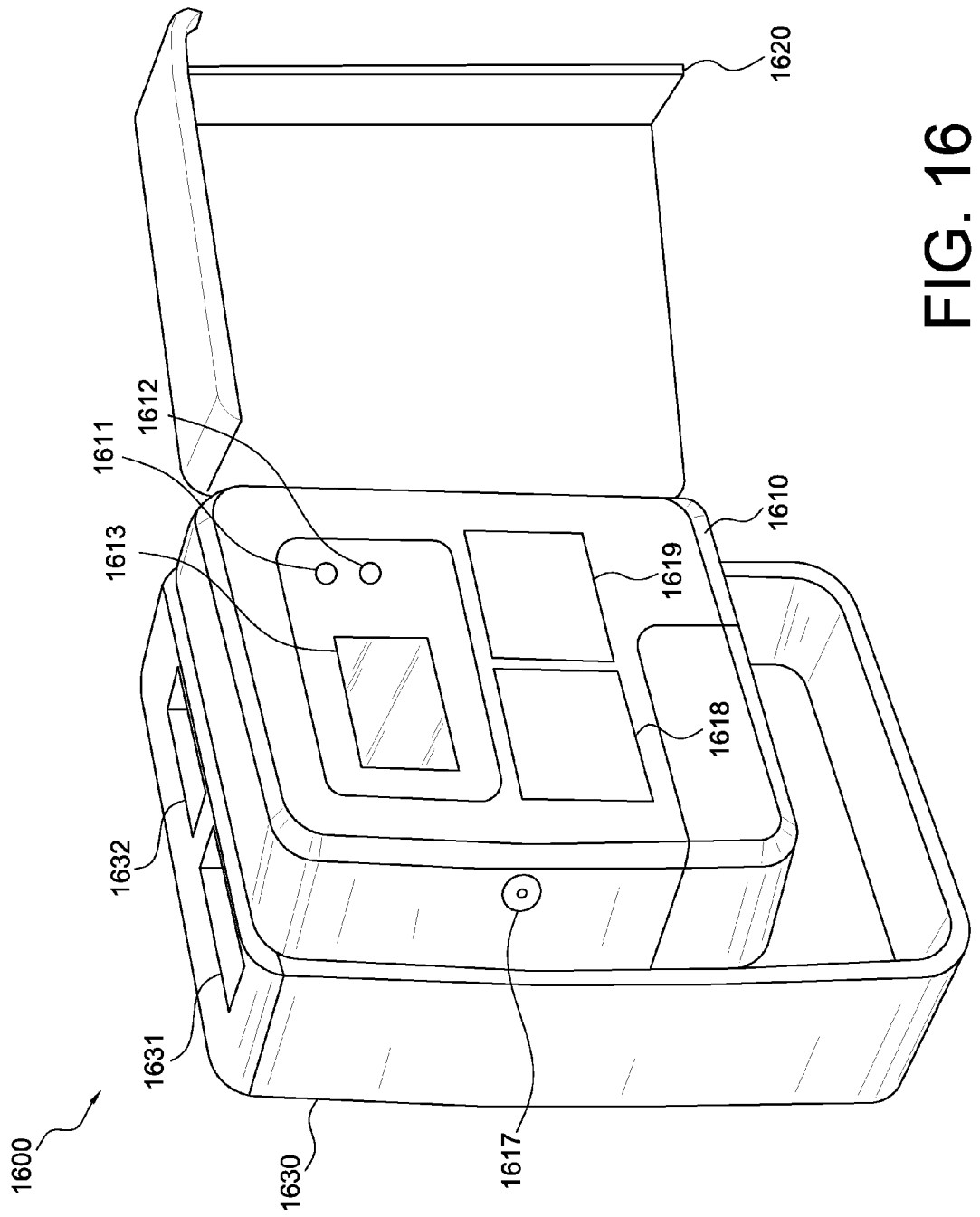
FIG. 16 illustrates a fifth alternative embodiment of a medicament storage case.

FIG. 16 illustrates a fifth alternative embodiment of a medicament storage case 1600. The fifth alternative embodiment 1600 includes a two-part case body 1610, 1630 that is hingedly attached to allow maintenance personnel to access the electronics after unlocking the front body 1610 from the rear body 1630 via the lock 1617. The fifth alternative embodiment 1600 also includes a Go button 1611, Stop button 1612, display device 1613, and hinged door 1620. As shown, the fifth alternative embodiment 1600 also includes two slots 1631, 1632 in the top surface for loading medicaments for dispensing. A medicament inserted into one of the slots 1631, 1632 falls through a channel until it is caught by a retaining structure; thereafter, the retaining structure may be actuated to release one of the medicaments. The fifth alternative embodiment 1600 also includes stickers 1618, 1619 including textual instructions.

According to the foregoing, various exemplary embodiments enable rapid access to medicaments that require prescription in emergency situations. For example, by providing a medicament storage case that enables the local user to communicate with a remote operator such as a health professional, remote qualified personnel may adequately assess the emergency situation and determine if an emergency prescription for the medicament is appropriate. Further, by providing a storage case that is remotely controlled by such personnel, the storage case may restrict access to the medicaments until such time that remote personnel enable access to the appropriate medicaments. Various other benefits will be apparent in view of the foregoing description.

It should be apparent from the foregoing description that various exemplary embodiments of the invention may be implemented in hardware and/or firmware. Furthermore, various exemplary embodiments may be implemented as instructions stored on a machine-readable storage medium, which may be read and executed by at least one processor to perform the operations described in detail herein. A machine-readable storage medium may include any mechanism for storing information in a form readable by a machine, such as a personal or laptop computer, a server, or other computing device. Thus, a machine-readable storage medium may include read-only memory (ROM), random-access memory (RAM), magnetic disk storage media, optical storage media, flash-memory devices, and similar storage media.

It should be appreciated by those skilled in the art that any block diagrams herein represent conceptual views of illustrative circuitry embodying the principals of the invention. Similarly, it will be appreciated that any flow charts, flow diagrams, state transition diagrams, pseudo code, and the like represent various processes which may be substantially represented in machine readable media and so executed by a computer or processor, whether or not such computer or processor is explicitly shown.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A medicament storage case assembly comprising:
    a case body defining a front surface, a rear surface, an internal area, and an opening in the front surface through which the internal area is accessible;
    securing hardware capable of securing the rear surface of the case body to a wall;
    a door hingedly connected to the case body adjacent the opening, wherein the door blocks access to the internal area when the door occupies a closed position and permits access to the internal area when the door occupies an open position;
    a medicament lock disposed within the internal area and configured to occupy a locked state and an unlocked state, wherein the medicament lock restricts removal of an epinephrine injector from the internal area when the medicament lock occupies the locked state and allows removal of the epinephrine injector from the internal area when the medicament lock occupies the unlocked state;
    an actuator configured to transition the medicament lock from the locked state to an unlocked state, wherein transitioning the medicament lock releases the epinephrine injector for removal from the internal area and subsequent use;
    a microphone configured to receive first audio as input from a local user;
    a speaker configured to output second audio to the local user;
    a communication unit configured to provide at least one communication channel to at least one remote site; and
    a processor configured to:
        establish, via the communication unit, a two way communication session between the local user and the remote site, wherein the communication unit transmits the first audio received by the microphone and receives the second audio to be output via the speaker, and
        receive an unlock signal that instructs the storage case to allow access to the epinephrine injector.

2. The medicament storage case of claim 1, wherein the processor is further configured to output an access signal to the actuator in response to receiving the unlock signal, wherein the actuator transitions the medicament lock from the locked state to the unlocked state in response to receiving the access signal.

3. The medicament storage case of claim 1, further comprising a button in communication with the processor, wherein the processor is configured to establish the two way communication session in response to the button being pressed.

4. The medicament storage case of claim 3, wherein the processor is further configured to:
 establish a landline telephone call via the communication unit and a plain ordinary telephone system (POTS) to an emergency dispatch in response to the button being pressed; and
 transmit predetermined information to the emergency dispatch via the landline telephone call.

5. The medicament storage case of claim 1, further comprising:
 a display device,
 wherein the processor is further configured to output video instructions via the display device to the user upon allowing access to the epinephrine injector.

6. The medicament storage case of claim 1, further comprising:
 a sleeve sized to contain the epinephrine injector and located within the internal area,
 wherein the medicament lock engages the sleeve in the locked state to restrict removal of the epinephrine injector from the internal area and disengages from the sleeve in the unlocked state to allow removal of the epinephrine injector from the internal area.

7. The medicament storage case of claim 6, wherein upon the medicament lock disengaging from the sleeve, the sleeve falls away from the medicament lock and toward the opening.

8. The medicament storage case of claim 1, further comprising an additional medicament lock configured to selectively restrict or allow removal of an additional epinephrine injector.

9. A medicament storage case comprising:
 a case body defining a front surface, a rear surface, an internal area, and an opening in the front surface through which the internal area is accessible;
 securing hardware capable of securing the rear surface of the case body to a wall;
 a door hingedly connected to the case body adjacent the opening, wherein the door blocks access to the internal area when the door occupies a closed position and permits access to the internal area when the door occupies an open position;
 a retaining structure configured to occupy a first state and a second state, wherein the retaining structure restricts removal of an epinephrine injector from the internal area when the retaining structure occupies the first state and allows removal of the epinephrine injector from the internal area when the retaining structure occupies the second state, wherein the retaining structure transitions from the first state to the second state in response to receiving an unlock signal;
 a microphone configured to receive first audio as input from a local user;
 a speaker configured to output second audio to the local user;
 a communication unit configured to provide at least one communication channel to at least one remote site; and
 a processor configured to:
  establish, via the communication unit, a two way communication session between the local user and the remote site, wherein the communication unit transmits the first audio received by the microphone and receives the second audio to be output via the speaker, and
  receive an access signal that instructs the storage case to allow access to the epinephrine injector.

10. The medicament storage case of claim 9, further comprising a processor configured to output the access signal to the actuator in response to receiving the unlock signal.

11. The medicament storage case of claim 9, further comprising a button in communication with the processor, wherein the processor is configured to establish the two way communication session in response to the button being pressed.

12. The medicament storage case of claim 11, wherein the processor is further configured to:
 establish a landline telephone call via the communication unit and a plain ordinary telephone system (POTS) to an emergency dispatch in response to the button being pressed; and
 transmit predetermined information to the emergency dispatch via the landline telephone call.

13. The medicament storage case of claim 9, further comprising:
 a display device,
 wherein the processor is further configured to output video instructions via the display device to the user upon allowing access to the epinephrine injector.

14. The medicament storage case of claim 9, further comprising:
 a sleeve sized to contain the epinephrine injector and located within the internal area,
 wherein the medicament lock engages the sleeve in the locked state to restrict removal of the epinephrine injector from the internal area and disengages from the sleeve in the unlocked state to allow removal of the epinephrine injector from the internal area.

15. The medicament storage case of claim 14, wherein upon the medicament lock disengaging from the sleeve, the sleeve falls away from the medicament lock and toward the opening.

16. A medicament storage case comprising:
 a case body defining a front surface, a rear surface, an internal area, a lower ledge, and an opening in the front surface through which the internal area is accessible;
 securing hardware capable of securing the rear surface of the case body to a wall;
 a door hingedly connected to the case body adjacent the opening, wherein the door blocks access to the internal area when the door occupies a closed position and permits access to the internal area when the door occupies an open position;
 a sleeve sized to contain an epinephrine injector and located within the internal area, the sleeve including a rail;
 a medicament lock comprising a hook movable between a first position and a second position, wherein the hook is positioned to engage the rail of the sleeve when in the first position and is positioned to disengage the rail of the sleeve when in the second position, and wherein the sleeve is suspended above the lower ledge when the hook is engaged with the rail of the sleeve and wherein the sleeve falls to the lower ledge when the hook disengages the rail of the sleeve;

an actuator comprising a solenoid, wherein the solenoid, upon activation, moves the hook from the first position to the second position;
a microphone configured to receive first audio as input from a local user;
a speaker configured to output second audio to the local user;
a communication unit configured to provide plain ordinary telephone system (POTS) connectivity and Internet connectivity;
a button accessible to the local user; and
a processor configured to:
  detect a press of the button,
  in response to detecting the press of the button:
    establish a telephone call to an emergency dispatch via the communication unit and the POTS,
    transmit predetermined information to the emergency dispatch via the telephone call, and
    establish a two-way communication between the local user and a remote site via the communication unit and the Internet, wherein the communication unit transmits the first audio received by the microphone and receives the second audio to be output via the speaker,
  receive an unlock message via the Internet, and
  in response to receiving the unlock message, cause activation of the solenoid to effect release of the sleeve.

17. The medicament storage case of claim 16, further comprising:
an additional sleeve including an additional rail;
an additional medicament lock engaged with the additional sleeve;
an additional solenoid configured to effect disengagement of the additional medicament lock from the additional sleeve;
wherein, in causing activation of the solenoid, the processor is configured to determine that the message is applicable to the sleeve and inapplicable to the additional sleeve.

18. The medicament storage case of claim 16, further comprising a detachable device connected to the case body, the detachable device comprising:
the microphone and the speaker; and
a WiFi device configured to transmit the video data to the processor.

19. The medicament storage case of claim 18, wherein:
the detachable device is selectively securable to the case body such that, when secured, the detachable device may not be detached from the case body; and
the processor is further configured to:
  receive, via the communication unit, an instruction to release the detachable device, and
  in response to the instruction to release the detachable device, effect release of the detachable device to allow a user to detach the detachable device from the case body.

20. The medicament storage case of claim 16, wherein the processor is further configured to transmit, via the communication module, an indication that the epinephrine injector has been dispensed.

21. The medicament storage case of claim 16, further comprising a temperature sensor for sensing temperature data, wherein the processor is further configured to transmit the temperature data via the communication module.

* * * * *